(12) United States Patent  
Subramanian et al.

(10) Patent No.: US 8,645,075 B2  
(45) Date of Patent: Feb. 4, 2014

(54) METHOD FOR PREDICTING ORGAN TOXICITY AND A SYSTEM THEREOF

(75) Inventors: Kalyanasundaram Subramanian, Bangalore (IN); Sowmya Raghavan, Bangalore (IN); Anupama Rajan Bhat, Bhavnagar (IN); Sonali Das, Murshidabad (IN); Jyoti Bajpai Dikshit, Bangalore (IN); Rajeev Kumar, Purnia (IN); Narasimha Mandyam Krishnakumar, Banglore (IN); Nalini Rajeshwara, Banglore (IN); Rajesh Radhakrishnan, Thiruvananthapuram (IN); Srivatsan Raghunathan, Pollachi (IN)

(73) Assignee: Strand Life Sciences PVT Ltd. (IN)

( * ) Notice: Subject to any disclaimer, the term of this patent is extended or adjusted under 35 U.S.C. 154(b) by 289 days.

(21) Appl. No.: 12/634,628

(22) Filed: Dec. 9, 2009

(65) Prior Publication Data

US 2010/0179798 A1    Jul. 15, 2010

Related U.S. Application Data

(60) Provisional application No. 61/153,422, filed on Feb. 18, 2009.

(30) Foreign Application Priority Data

Dec. 10, 2008    (IN) .......................... 03091/CHE/2008

(51) Int. Cl.  
*G06F 7/00*    (2006.01)

(52) U.S. Cl.  
USPC .................. 702/19; 702/20; 703/11; 703/12; 703/13; 707/700

(58) Field of Classification Search  
None  
See application file for complete search history.

(56) References Cited

U.S. PATENT DOCUMENTS 7,853,406 B2    12/2010    Michelson et al.

OTHER PUBLICATIONS

Chirugi et al. (2007) PLOS Computational Biology vol. 3 Issue 9 p. 1801-1806.*  
Kinugasa, T., "Effect of Bile Duct Ligation on Bile Acid Metabolism in Rats," Journal of Lipid Research, 1981, pp. 201-207, vol. 22.  
Subramanian, K. et al., "A Systems Biology Based Integrative Framework to Enhance the Predictivity of in Vitro Methods for Drug-induced Liver Injury," Expert Opinion Drug Safety, 2008, 7(6): pp. 647-662.  
Watanabe, N., "Motility of Bile Canaliculi in the Living Animal: Implications for Bile Flow," The Journal of Cell Biology, Jun. 1991, pp. 1069-1080, vol. 114, No. 5.

* cited by examiner

*Primary Examiner* — Mary Zeman  
(74) *Attorney, Agent, or Firm* — Fenwick & West LLP

(57) ABSTRACT

The attached disclosure provides a systems approach based on mathematical modelling of the kinetics of essential biochemical pathways involved in organ homeostasis. When this in silico model is coupled with in-vitro and/or in-vivo measurements to quantify drug-induced perturbations, a powerful platform that allows accurate and mechanistic-level prediction of drug-induced organ injury can be generated. The method described in this disclosure demonstrates that several physiological situations can also be accurately modelled in addition to the effect of perturbations induced by drugs. It can also be used along with high-throughput "omics" data to generate testable hypotheses leading to informed decision-making in drug development.

8 Claims, 11 Drawing Sheets

Figure 1:
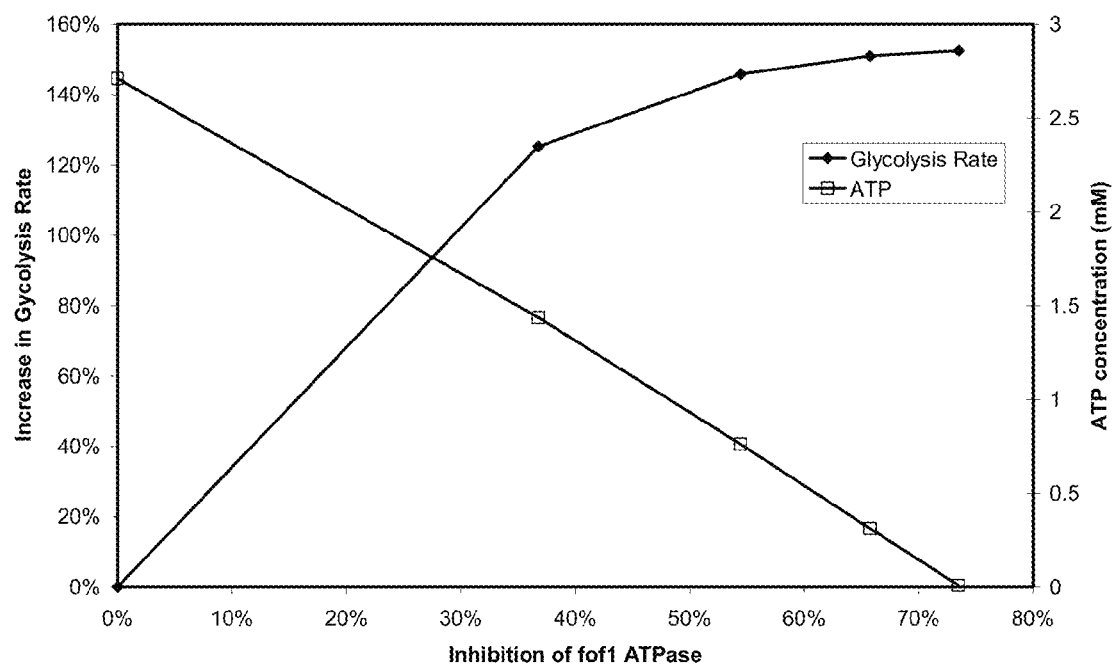

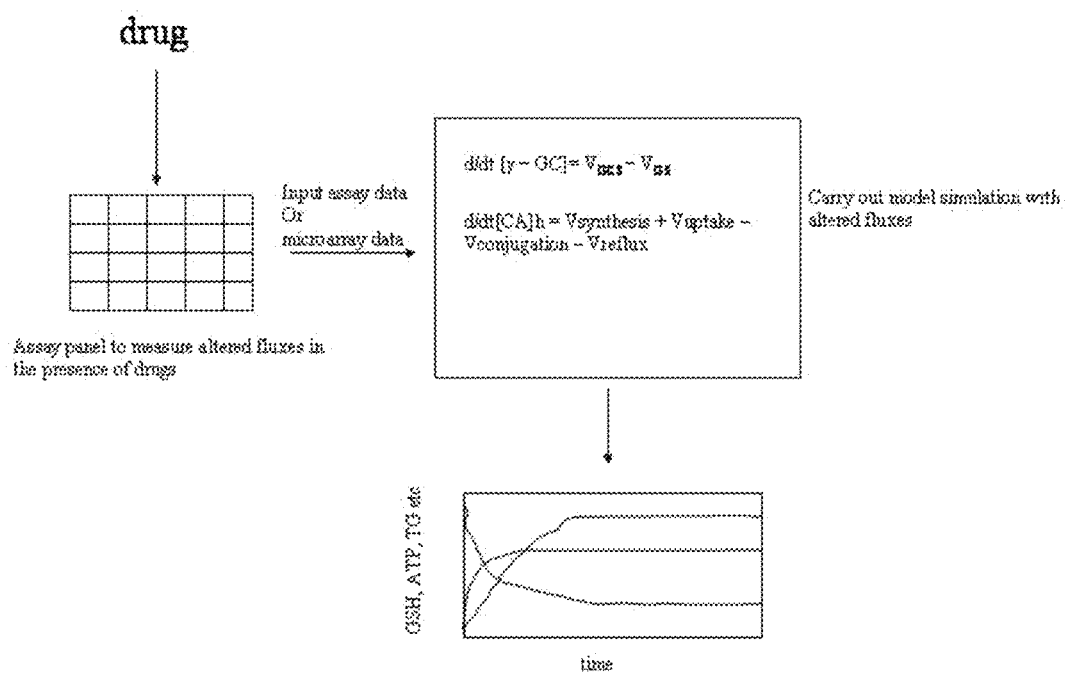
Figure: 7

Figure: 8

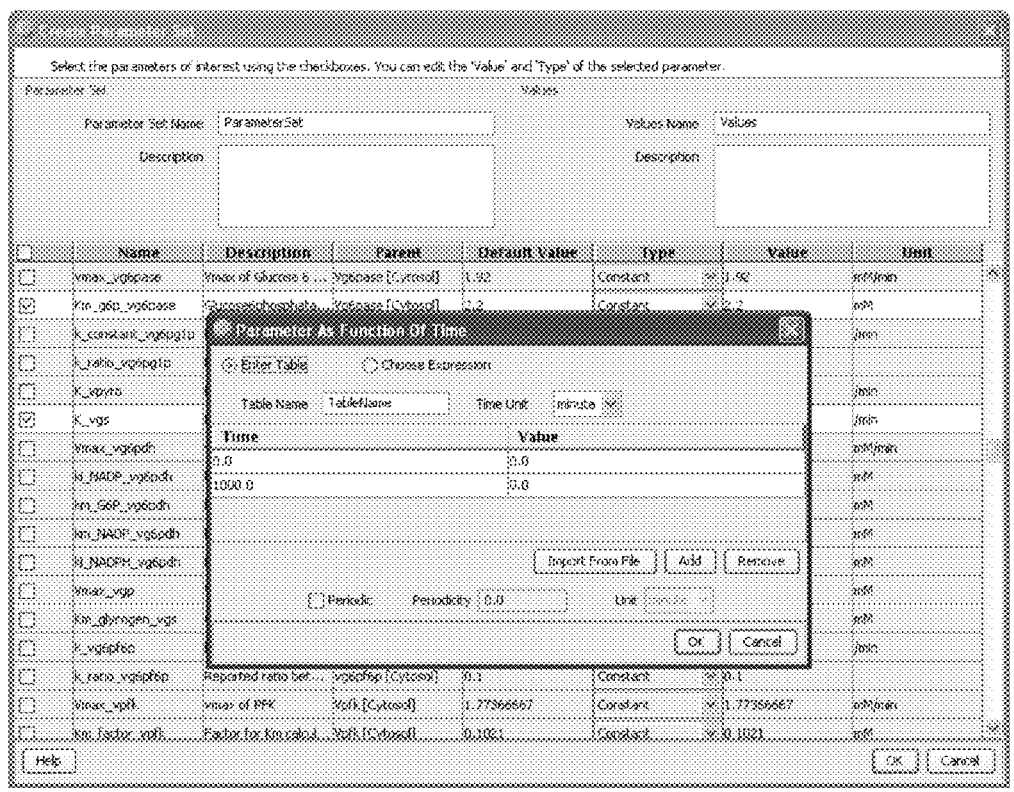
Figure: 9

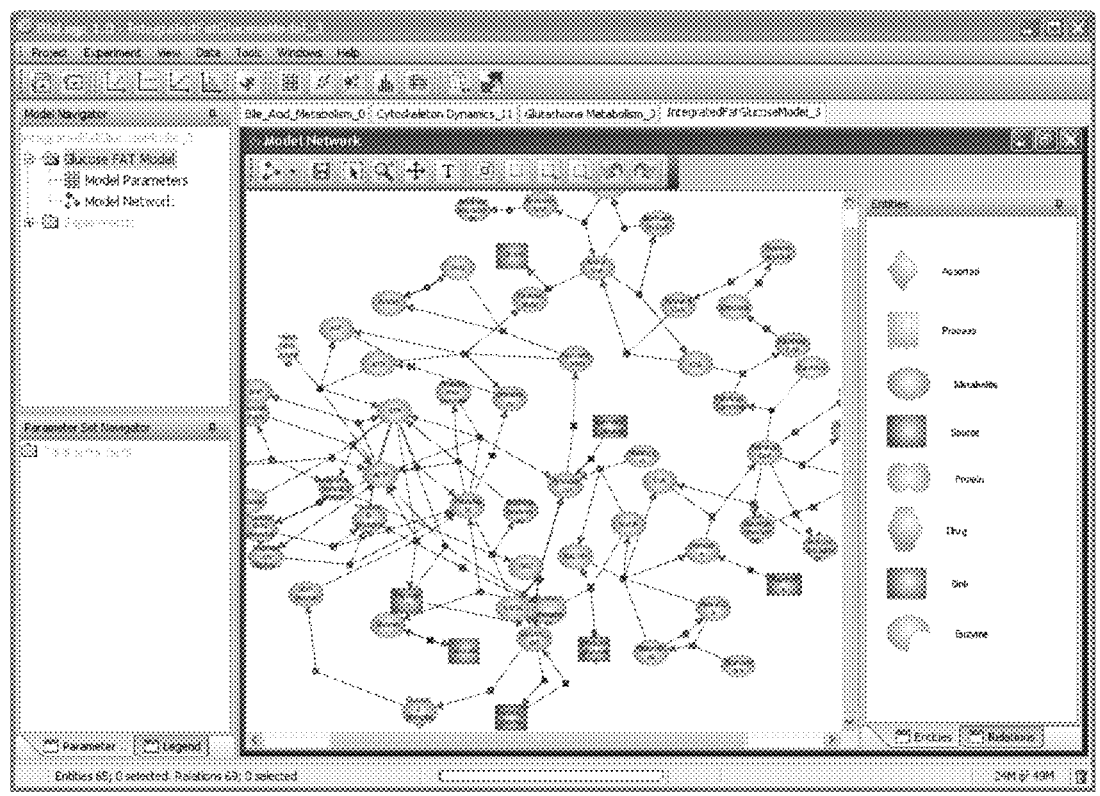
Figure: 10

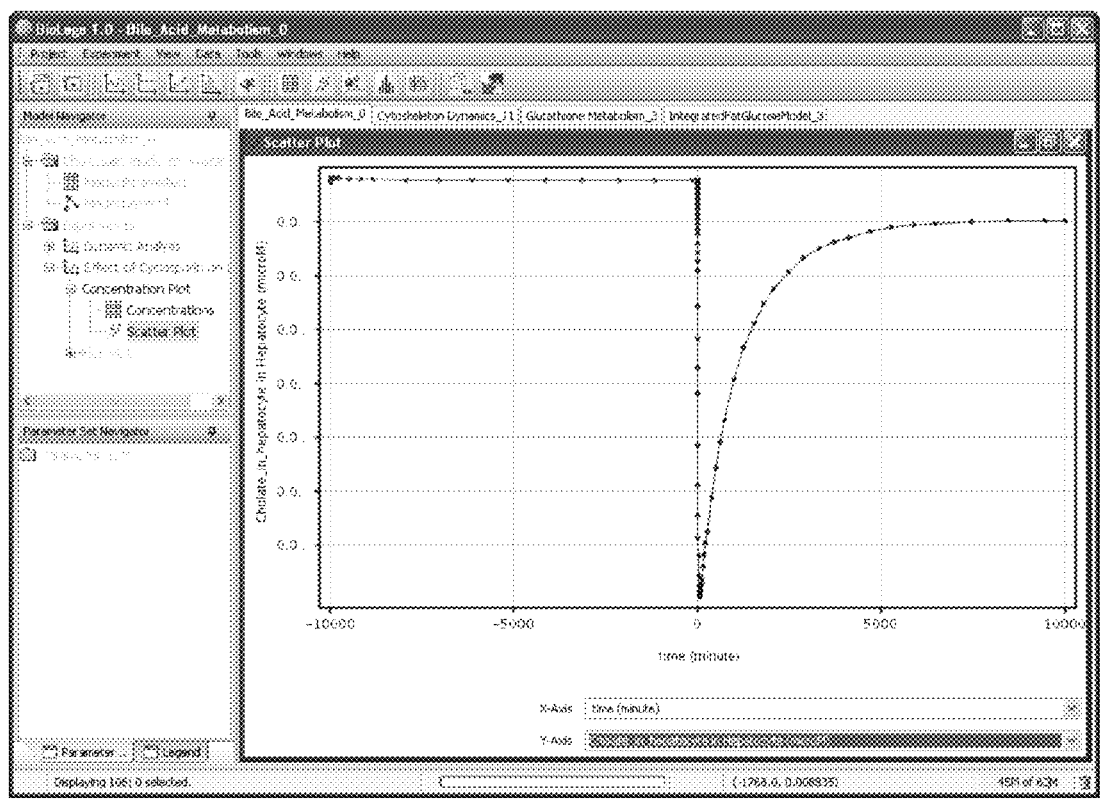
Figure: 11

METHOD FOR PREDICTING ORGAN TOXICITY AND A SYSTEM THEREOF

CROSS-REFERENCE TO RELATED APPLICATIONS

The present application claims priority from India provisional Application No. 03091/CHE/2008, filed on Dec. 10, 2008, entitled "A Method For Predicting Organ Toxicity And A System Thereof", and further claims priority from U.S. provisional application Ser. No. 61/153,422, filed Feb. 18, 2009, entitled "A Method For Predicting Organ Toxicity And A System Thereof", both of which are incorporated herein by reference in their entirety.

TECHNICAL FIELD

The present disclosure is in relation to prediction of organ toxicity. In addition, the present disclosure provides a method and a system for prediction of organ toxicity.

BACKGROUND AND PRIOR ART

Failures in pre-clinical drug development are largely attributable to poor pharmacokinetics and toxicity. Successful drug development hence requires good model systems whose results can be reliably extrapolated to humans in the clinic. Recently, we have developed predictive QSAR models based on advanced machine learning algorithms that perform fairly well in the prediction of pharmacokinetic properties. However, QSAR based models are limited in their ability to generalise out of the training-set chemical space. Some in vitro methods provide reasonable correlations with in vivo pharmacokinetics, but important exceptions such as the substituted anthracyclines, where large variability in properties result from simple substitutions, stress the need for improved testing methods. Over the last decade there has been a steady improvement in pharmacokinetic prediction leading to reduction in failures.

The post-marketing withdrawal of drugs is often due to their toxicity. It is observed that toxicity is often associated with biotransformation. This is carried out mainly by a family of enzymes called cytochrome P450s that exhibits great inter-species variations and has also been associated with the development of idiosyncratic drug toxicity in humans. Due to the abundance of these enzymes in the liver and due to its portal location in the body, drug-induced liver injury (DILI) is a major cause for drug withdrawal. Since about half of the liver failures are due to drug exposure, methods that enable reliable prediction of DILI are critical. However, injury to the liver in humans cannot be extrapolated from toxicity in rodents due to metabolic differences. In preclinical development, hepatic intrinsic clearance is measured using microsomes to rank molecules in order of their metabolic stability. Although methods that use human microsomal extracts in combination with rat hepatocytes in vitro are available, they are of limited value and quite cumbersome to use. In addition, they are ineffective in their ability to discern the potential for idiosyncratic toxicity. More recently, studies based on whole genome approaches are becoming increasingly common. These suffer from the need to use high doses to invoke detectable transcriptional responses. In addition, they are unable to predict toxicity that arises due to responses that are non-transcriptional in origin. This is exemplified by perhexylline, which is known to induce steatosis but does not conform to the gene expression of another steatotic compound, amiodarone.

The pressing need is for an approach that integrates many facets of toxic pathways to the chemical structure in a systematic manner to provide detailed mechanistic rationale for toxicity as well as potential biomarkers for detection. Such an approach carries the potential to jumpstart the area of toxicity prediction which has remained stagnant without significant breakthroughs. In this article, we describe how we have developed a system approach to model pathways in the liver in silico, which can be used in combination with in vitro measurements. This can be used to create a detailed predictive platform capable of providing insights into how drugs injure the liver. Our systems approach is based on the principle that if we are able to model normal behaviour of the liver, i.e. homeostasis, we can explain toxicity as perturbations of this normal system. This approach allows us to model the biology independent of the action of any drug and allows us to design a predictive system that can generalise and is not limited by "training space".

In the field of our disclosure, several QSAR based models are available for user-defined toxic endpoints. These are limited applications since they tend to be specific to the training-set's chemical space. Some in vitro methods provide reasonable correlations with in vivo pharmacokinetics. However, not all of them are able to address issues where large differences in properties result from simple substitutions in chemical entities. Hence, improved testing methods are necessary. Toxicogenomic methods also are being used but are unable to address situations where the toxicity is not associated with transcriptional changes.

In terms of problems our disclosure addresses, our disclosure dispenses with the notion of training space. While in the present incarnation, it focuses on the liver, it can be applied to any organ system or type of toxicity provided an appropriate steady state can be defined. Our system provides a mechanistic understanding of the toxicity and the key biochemical event(s) that is/are being perturbed.

Organ toxicity is a complex phenomenon which can be caused due to multiple biological components being affected. QSAR models cannot capture such complexity. The other main drawback of QSAR based models is that of the training set. The model's performance is only as good as the training set that it is trained on. Whenever, examples different from the training set are considered, the QSAR models run into limitations. Our disclosure dispenses with the notion of training set. The model is also a generic model of cell survival and can be applied to various organs as well with appropriate changes in the kinetics of the enzymes. Its wide applicability is due to the systems approach used whereby toxicity and other unrelated disease states can be analysed with equal facility.

OBJECTIVES OF THE PRESENT DISCLOSURE

First objective of the present disclosure is to provide a method for predicting organ toxicity.

Second objective of the present disclosure is to provide a system for prediction of organ toxicity.

Third objective of the present disclosure is to provide a method to obtain an in silico model of an organ.

Fourth objective of the present disclosure is to provide an in silico model of an organ.

Fifth objective of the present disclosure is to provide a method to design assays.

SUMMARY

Accordingly, the present disclosure relates to a method for predicting organ toxicity comprising steps of: listing of drug-induced organ injuries, obtaining molecular mechanisms of toxicity followed by tabulating underlying biochemical pathways of said drugs which precipitates organ injury, identifying biomolecules, inferring biochemical pathways and modeling kinetics of enzymes involved in these pathways to obtain a homeostatic in silico model, perturbing the model and designing assays to measure the perturbation, applying the assays to a chemical or set of chemicals to generate new assay data, and feeding the new assay data to the model for predicting toxicity and organ damage; a system for predicting organ toxicity said system comprising: storage element having list of drug-induced organ injury along with their molecular mechanisms of toxicity and underlying biochemical pathways, in silico model component configured to represent normal organ, in vitro assays designed to quantitatively measure the perturbations that injure an organ, means to feed assay data obtained from in vitro analysis into in silico model and an interface to output results for predicting organ toxicity; a method to obtain an in silico model of an organ, comprising steps of: listing of drug-induced organ injuries, obtaining molecular mechanisms of toxicity followed by tabulating underlying biochemical pathways of said drugs precipitates organ injury and identifying biomolecules, infering biochemical pathways and modeling kinetics of enzymes involved in these pathways to obtain a homeostatic in silico model; an in silico model of an organ comprising: molecular mechanisms and biochemical pathways of drug-induced perturbations, biomolecules and modeled kinetics of enzymes involved in the biochemical pathways and formulating the above data, to obtain an in silico model; a method to design in vitro assays comprising steps of: listings of drug-induced organ injury, obtaining molecular mechanisms of toxicity followed by tabulating underlying biochemical pathways of said drugs which precipitates organ injury, identifying biomolecules, their concentration ranges that correlate with toxicity after exposure to drugs, infering biochemical pathways and modeling kinetics of enzymes involved in these pathways to obtain a homeostatic in silico model and perturbing the model, inferring perturbations in the model that lead to toxicity and designing assays.

BRIEF DESCRIPTION OF THE ACCOMPANYING DRAWINGS

FIG. 1 Inhibition of fof1ATPase causes a compensatory increase in the rate of glycolysis to maintain ATP levels in the hepatocyte. However, this increase cannot fully compensate for the loss in ATP generation capacity resulting eventually in depletion ATP in the hepatocyte.

Figure 2:
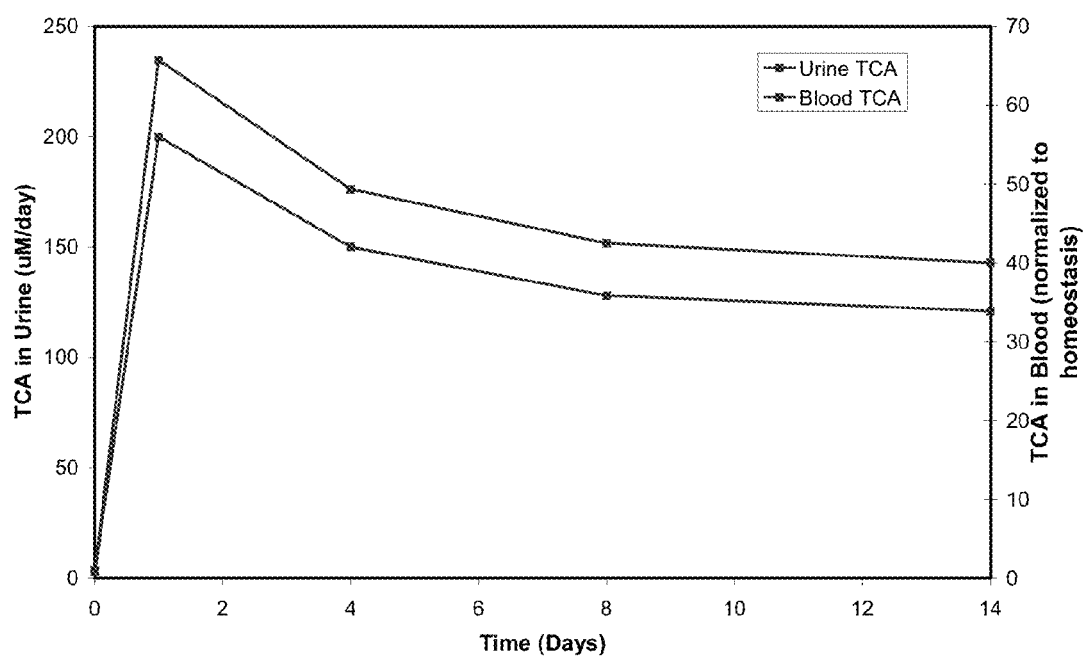

FIG. 2 Bile duct ligation results in increase in bile salt levels in the blood and urine that slowly begins to reduce back over a 14 day period.

Figure 3:
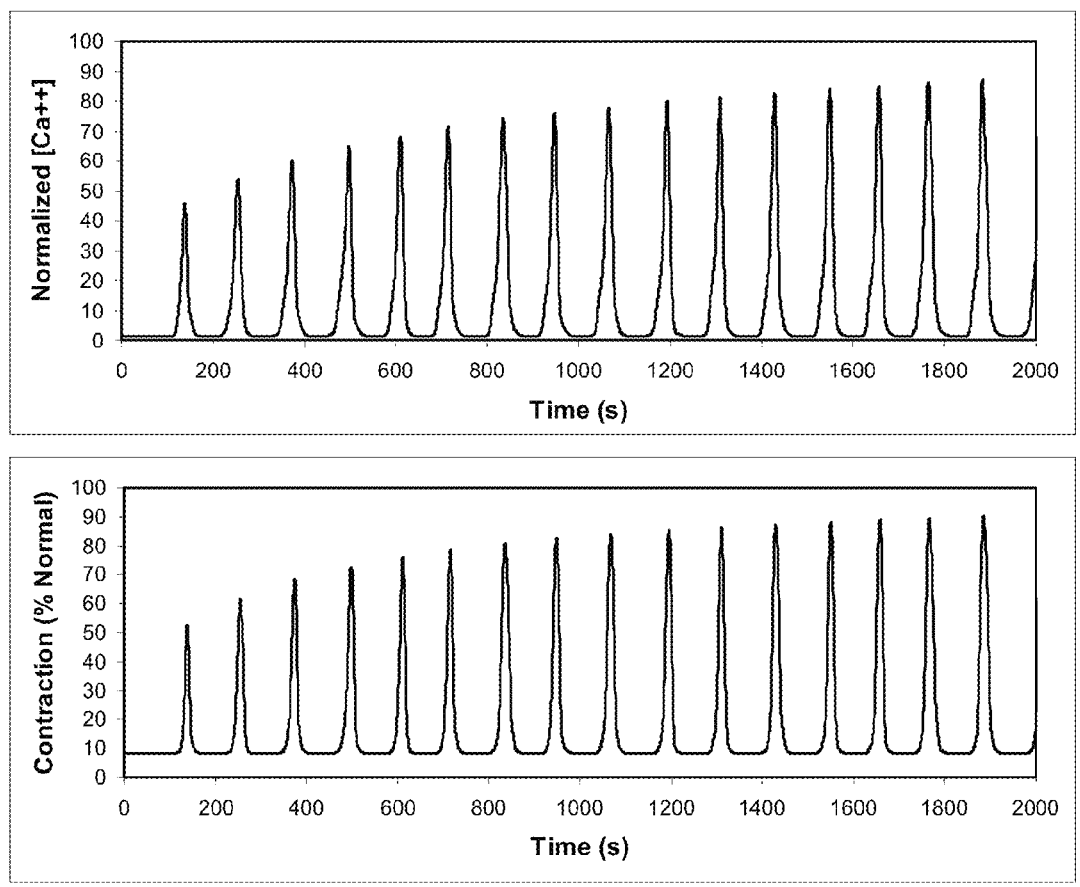

FIG. 3 Increase in vasopressin levels result in a periodic increase in intracellular calcium ion concentration which eventually results in increased contractility of the canaliculus.

Figure 4:
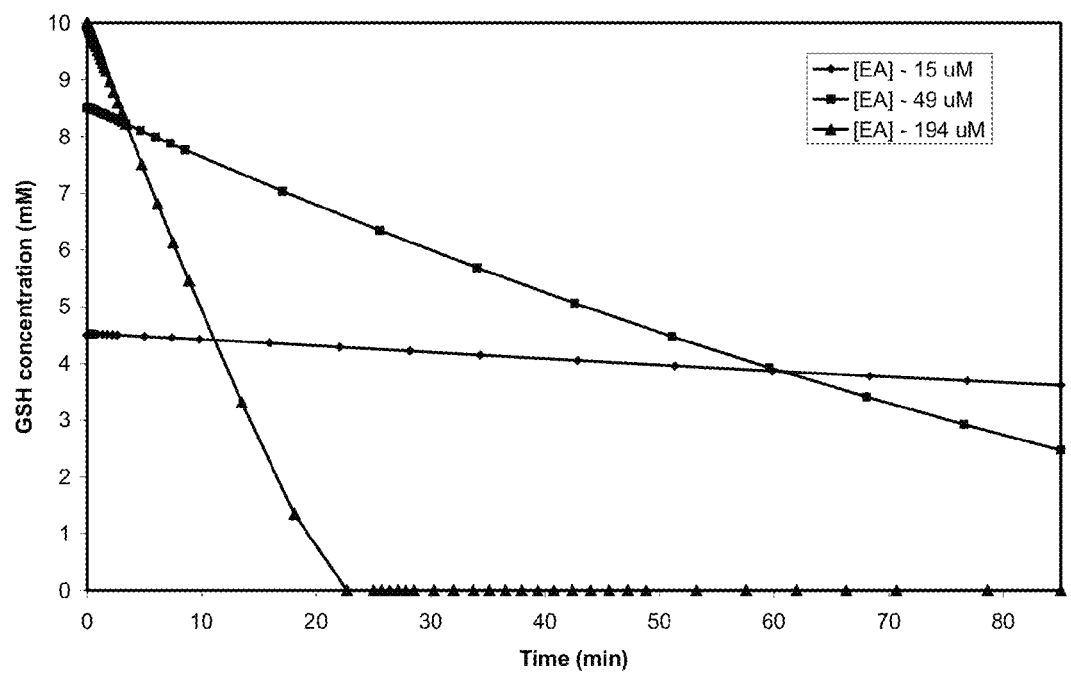

FIG. 4 Simulation showing the impact of perfused ethacrynic acid on the intracellular levels of glutathione, the simulation results match the experimental data.

Figure 5:
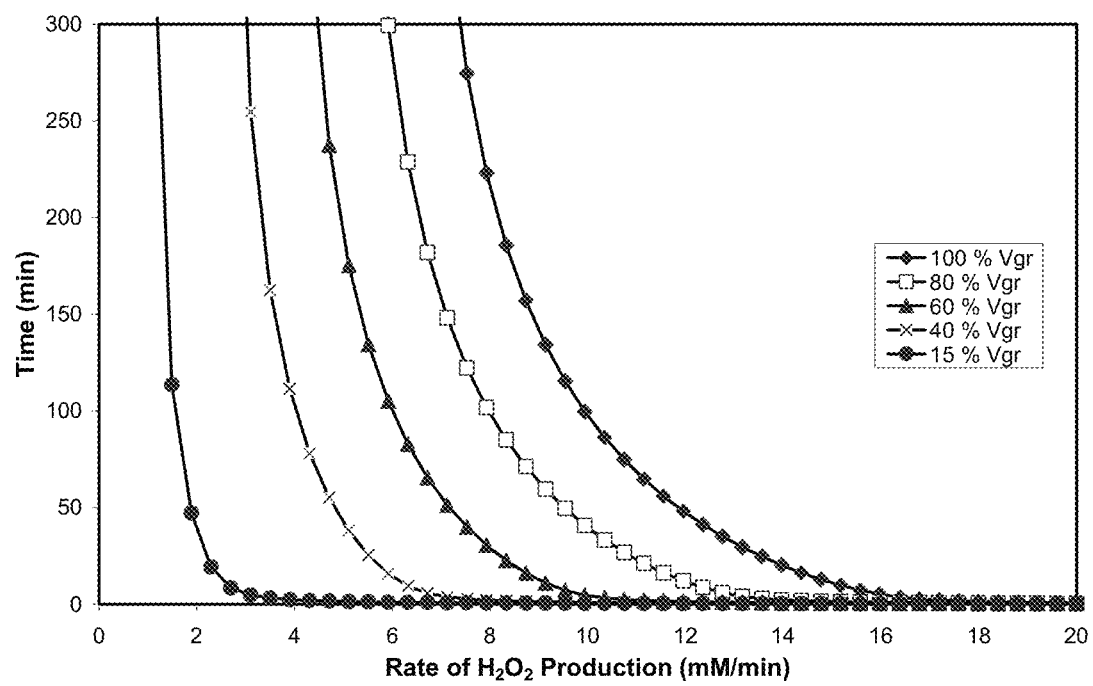

FIG. 5 Simulation showing individual variations in time to deplete intracellular glutathione upon increase in $H_2O_2$ production due to variations in the glutathione-reductase activity (Vgr).

Figure 6:
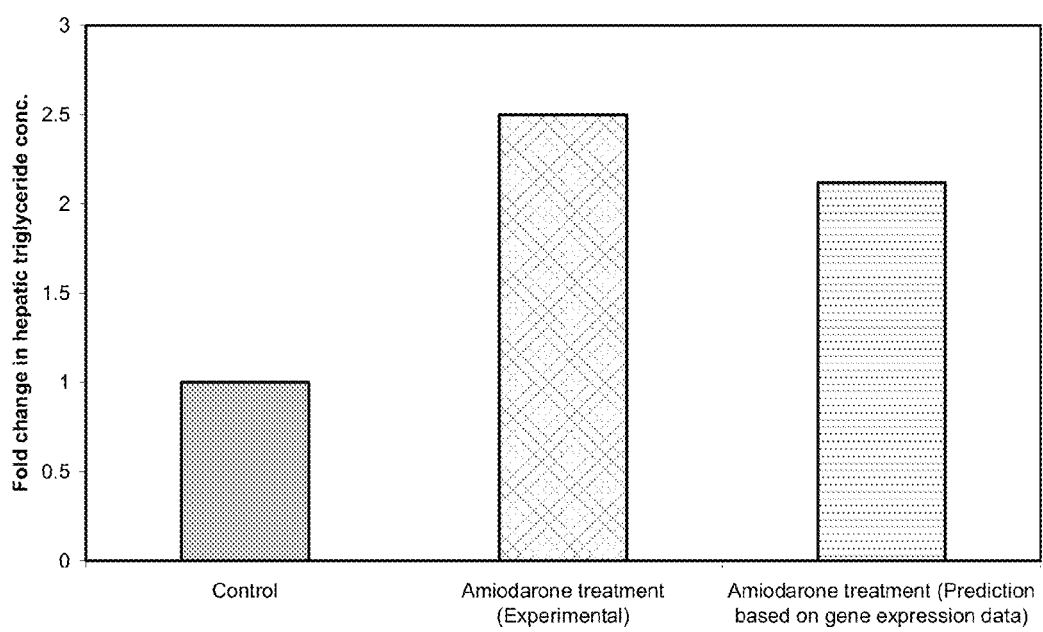

FIG. 6 Simulation predicting the effect of amiodarone on intracellular triglyceride concentration. The predictions of the model (horizontal lines) are in excellent concordance with experimentally measured levels (cross-hatched).

FIG. 7 Model work flow.

Figure 8:
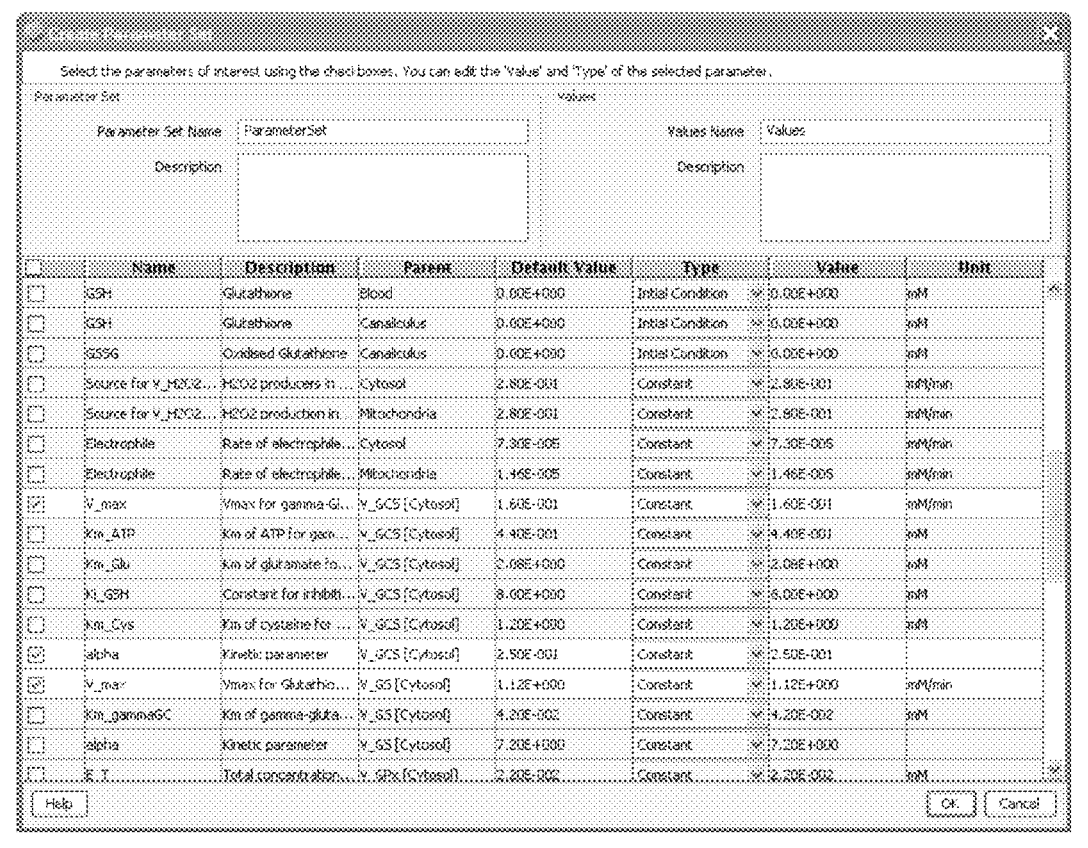

FIG. 8 Screen shot showing table of inputs and parameters.

FIG. 9 Screen shot showing pop-up window that allows that allows the parameter value to be a function of time.

FIG. 10 Screenshot of interface used to map and model the entities relationships.

FIG. 11 Screenshot showing graphic output from platform interface.

DETAILED DESCRIPTION

The present disclosure relates to a method for predicting organ toxicity comprising steps of: listing of drug-induced organ injuries; obtaining molecular mechanisms of toxicity followed by tabulating underlying biochemical pathways of said drugs which precipitates organ injury; identifying biomolecules, inferring biochemical pathways and modeling kinetics of enzymes involved in these pathways to obtain a homeostatic in silico model; perturbing the model and designing assays to measure the perturbation; applying the assays to a chemical or set of chemicals to generate new assay data; and feeding the new assay data to the model for predicting toxicity and organ damage.

In an embodiment of the present disclosure, said organ is selected from a group comprising but not restricted to liver, kidney, pancreas lung, heart, skin, eye, intestine, spleen and brain.

In an embodiment of the present disclosure, said listings are performed from a group comprising textbooks and clinical literature.

In an embodiment of the present disclosure, said molecular mechanisms are obtained from literature.

In an embodiment of the present disclosure, said organ injuries could also be due to chemicals and/or toxins.

In an embodiment of the present disclosure, said biomolecule concentration ranges determine safe physiological limits.

In an embodiment of the present disclosure, said biomolecule concentration ranges is correlated with toxicity after exposure to drugs.

In an embodiment of the present disclosure, said modeling kinetics of enzymes is performed to maintain physiological limits of critical metabolites.

In an embodiment of the present disclosure, said assay data is generated by in-vitro and/or in-vivo methods.

In an embodiment of the present disclosure, the model can be either an individual model or combined model for organ diseases.

In an embodiment of the present disclosure, the model is either individual model or combined model preferably for liver necrosis, liver steatosis and cholestasis.

In an embodiment of the present disclosure, said methods are designed to measure perturbations leading to any individual or combined forms of disease states.

In an embodiment of the present disclosure, said method is either used singly or in combination for abnormal liver function tests resulting from drug or chemical exposure.

In an embodiment of the present disclosure, the assay data is fed into the model using simulator applications.

In an embodiment of the present disclosure, the toxicity can be measured quantitatively.

The present disclosure relates to a system for predicting organ toxicity said system comprising: storage element having list of drug-induced organ injury along with their molecular mechanisms of toxicity and underlying biochemical pathways; in silico model component configured to represent normal organ; in vitro assays designed to quantitatively measure the perturbations that injure an organ; means to feed assay data obtained from in vitro analysis into in silico model; and an interface to output results for predicting organ toxicity.

In an embodiment of the present disclosure, the in silico model is configured to represent normal organ.

In an embodiment of the present disclosure, the in silico model component is the representation of a minimal set of biochemical networks underlying organ cell viability.

The present disclosure relates to a method to obtain an in silico model of an organ, comprising steps of: listing of drug-induced organ injuries; obtaining molecular mechanisms of toxicity followed by tabulating underlying biochemical pathways of said drugs precipitates organ injury; and identifying biomolecules, infering biochemical pathways and modeling kinetics of enzymes involved in these pathways to obtain a homeostatic in silico model.

In an embodiment of the present disclosure, said listings are performed from a group comprising text books and clinical literature.

In an embodiment of the present disclosure, said molecular mechanisms are obtained from literature.

In an embodiment of the present disclosure, said biomolecule concentration ranges determine safe physiological limits.

In an embodiment of the present disclosure, said modeling kinetics of enzymes is performed for maintenance of physiological limits.

In an embodiment of the present disclosure, said biomolecule concentration ranges is correlated with toxicity after exposure to drugs.

In an embodiment of the present disclosure, the model can be either individual model or combined model for organ diseases.

The present disclosure relates to an in silico model of an organ comprising: molecular mechanisms and biochemical pathways of drug-induced perturbations; biomolecules and modeled kinetics of enzymes involved in the biochemical pathways; and formulating the above data, to obtain an in silico model.

In an embodiment of the present disclosure, the molecular mechanisms are obtained from literature and biochemical pathways are tabulated.

In an embodiment of the present disclosure, the in silico model is a homeostatic model.

The present disclosure relates to a method to design in vitro assays comprising steps of: listings of drug-induced organ injury; obtaining molecular mechanisms of toxicity followed by tabulating underlying biochemical pathways of said drugs which precipitates organ injury; identifying biomolecules, their concentration ranges that correlate with toxicity after exposure to drugs, infering biochemical pathways and modeling kinetics of enzymes involved in these pathways to obtain a homeostatic in silico model; and perturbing the model, inferring perturbations in the model that lead to toxicity and designing assays.

In an embodiment of the present disclosure, the in silico model perturbation is done by altering various properties of the enzymes in the relevant biochemical pathways.

In another embodiment of the present disclosure details a novel methodology for the prediction of hepatotoxicity. It is comprised of two essential components and a software interface. The first is the model component, which is a mathematical representation of a minimal set of biochemical networks underlying liver cell viability that are necessary to represent a normal liver. The second is the assay component which is a set of biochemical assays to measure perturbations of this normal state. Together, the two components form the predictive platform for hepatotoxicity. The software provides a user interface for analysis and output of results.

The predictive platform was constructed as follows.
1. All major forms of drug-induced liver injury were listed from texts and clinical literature.
2. The molecular mechanisms of toxicity that corresponded to these forms of toxicity were then obtained through an extensive literature survey.
3. The underlying biochemical pathways that must suffer derangement in order to precipitate such liver injury were then tabulated (Table 1).
4. All these information's are then stored in a computer readable format in storage element. For example, as files and folders from which these data could be read or accessed. These information could also be stored in a database as well.
5. Next, we identified the key biomolecules whose concentration ranges determine safe physiological limits.
6. We then modelled the kinetics of the key enzymes involved in the pathways for the maintenance of these safe ranges.
7. We then set up a system of nonlinear ordinary differential equations of the following general form.

Rate of change of metabolite concentration=rate of synthesis of the metabolite–rate of utilization of the metabolite.

This system of differential equations was solved numerically and at steady state reproduced homeostasis—a state that describes the normal behaviour of the liver as measured by the concentrations of various metabolites and rates of processes.

8. We then perturbed the model in various ways, either to mimic the interactions of drugs with the underlying biochemistry of the liver or to represent other forms of damage to the liver, such as a complete blockage of the bile-secretory apparatus, increased energy demand, increased oxidative stress etc. These interactions were simulated mathematically, and allowed us to reproduce published observations of toxicity and liver damage.
9. Starting from the homeostasis described by the model we performed parameter sensitivity analyses to identify pathways and processes that perturbed the system significantly. This computational "mining" allowed us to design in vitro assays that measure the impact of a drug on the pathways, enzymes and processes that had the greatest potential impact on the homeostasis of the liver. A working example of the method is described in FIG. 7. The prototype model uses the kinetics of rat liver enzymes, but in principle, is applicable to human counterparts as well.

TABLE 1

Components of the systems model of hepatotoxicity

| Form of liver toxicity | Model component | Underlying biochemical processes |
|---|---|---|
| Necrosis | Energy metabolism | Synthesis of ATP via glycolyis and oxidative phosphorylation; ATP utilization |
| Necrosis | Glutathione metabolism | Synthesis of glutathione, transport of glutathione, glutathione conjugation, detoxification of hydrogen peroxide |

TABLE 1-continued

Components of the systems model of hepatotoxicity

| Form of liver toxicity | Model component | Underlying biochemical processes |
|---|---|---|
| Steatosis | Fatty acid and triglyceride metabolism | Uptake, synthesis and beta oxidation of fatty acid, triglyceride synthesis and export |
| Cholestasis | Bile acid metabolism and transport | Uptake, synthesis and secretion of bile salts; mechanisms involved in canalicular contractility. |

The FIG. 7 shows an application of the model. As mentioned above, the model and the assays together can be used to predict the hepatotoxic potential of a NCE (new chemical entity). The assays are to be performed in vitro with the NCEs. The results of the assays are then to be input to the model using simulation software such as BioLego. The other modeling and simulation softwares are PhysioLab, Jdesigner, Celldesigner, COPASI and SimBiology. The results of the model simulations can then be interpreted and conclusions drawn about the toxic potential of the NCE. FIGS. 8 to 11 show various screen shots pertaining to the present disclosure.

The present disclosure applies to the major forms of toxicity, namely, steatosis, necrosis and cholestasis. It is not applicable to immune-mediated events that occur in some forms of toxicity or to injury that damages the supporting architecture of the liver. In the present form it is applicable to rat and human livers only. In addition to assay data, microarray gene expression data can also be used with the model to make testable predictions.

We defined the scope of the systems-based liver injury prediction platform with the following questions:
1. Can liver functions be accurately represented by a collection of biochemical pathways?
2. Can this collection be mathematically modelled using kinetic data to mimic normal homeostasis?
3. Can toxicity be represented as a set of perturbations of this homeostasis?
4. Can multiple mechanisms of toxicity be understood using this framework?
5. Can we discover mechanism-specific biomarkers to predict toxicity from this approach?

In summary, the present disclosure extensively lists the liver disorders, the drug induced liver injuries (toxicity) and the molecular mechanisms underlying the disease states are determined. The biochemical pathways governing and responsible for the disease conditions are elucidated using the information generated from the molecular mechanisms. Thereafter, the kinetics of important enzymes and the concentrations of important biomolecules are determined. This information is used to determine the steady state of the system or Homeostasis, which in a way also represents the normal healthy liver. Now this homeostasis is perturbed or disturbed in order to mimic disease conditions or conditions related to drug toxicity. Thereafter, parameter sensitivity analysis is carried out with respect to the changes in homeostatic condition and based on this, a set of in-vitro assays are designed. The data generated from these assays is then fed into the model and simulations are carried out using the software interfaces such as Biolego, PhysioLab, Jdesigner, Celldesigner, COPASI and SimBiology. The results from the simulation are then compared with experimental results. These in-turn are checked for their accordance with the existing literature wherever possible. If the data generated are in accordance with each other, we conclude that the platform including the assays and in-silico model can be successfully used to predict toxicity or organ damage due to various diseases.

The role of the software is to provide an easy interface for carrying out simulations of the model. The assays measure the change in the functioning of key enzymes in the biochemical network modeling. This change is fed into the model using the software and the outcome (in vivo behavior) simulated.

The same software is capable of being applied under other disease conditions. The software is thus capable of visually displaying the results of the model which could be manipulated in many ways. If the manipulations are carried out using drugs and the model is a liver model, then hepatotoxicty can be predicted. If the manipulations are carried out using drugs and the model is that of a kidney, then nephrotoxicity can be predicted. If the manipulations pertain to any other disease such as diabetes, then the fate of the disease can be predicted.

The technology of the present application is further elaborated with the help of following examples. However, the examples should not be construed to limit the scope of the disclosure.

Example: 1

At the outset we conducted a literature survey to generate a fairly comprehensive list of hepatotoxic drugs and toxins. We then compiled the mechanisms by which such drugs injured the liver. Some examples of drugs are—diclofenac, which induces oxidative stress, chlorpromazine, which causes cholestasis, acetaminophen that causes necrosis, etc. Subsequently, we assembled the underlying biochemical pathways that must suffer derangement in order to precipitate such liver injury. For the examples listed above, these would be antioxidant metabolism, bile salt synthesis and secretion and ATP homeostasis respectively. We focused on the processes in the liver involved in lipid, bile, energy and antioxidant metabolism in detail. We then modelled the kinetics of the key enzymes involved in these pathways and set up a system of nonlinear ordinary differential equations. These equations were of the following general form.

Rate of change of metabolite concentration=rate of synthesis of the metabolite−rate of utilization of the metabolite.

The resultant structure of the model is briefly described in Table 1 and details of the model equations provided in subsequent portions of the specification. This system of differential equations was solved numerically and at steady state reproduced homeostasis, a state that describes the normal behaviour of the liver as measured by the concentrations of various metabolites and fluxes of processes. The advantage of this approach is that since we modeled essential biochemical phenomena, a generally applicable predictive system was built even though an exhaustive list of hepatotoxic drugs was not used.

We then perturbed the model in various ways, either to mimic the interactions of drugs with the underlying biochemistry of the liver or to represent other forms of damage to the liver, such as a complete blockage of the bile-secretory apparatus, increased energy demand, increased oxidative stress etc. These interactions were simulated mathematically, and allowed us to reproduce published observations of toxicity and liver damage. Starting from the homeostasis described by the model we performed parameter sensitivity analyses to identify pathways and processes that perturbed the system significantly. This computational "mining" allowed us to design in vitro assays that measure the impact of a drug on the pathways, enzymes and processes that had the greatest potential impact on the homeostasis of the liver. In the prototype model we focused on the kinetics of rat liver enzymes, but are now extending this approach to human counterparts as well.

Example: 2

The model was tested under various physiological and pathophysiological conditions for its predictivity. Some of these simulations are described in this section.

Ability of the model to reproduce homeostasis: The model predictions at steady state were compared with published data on the levels of metabolites and fluxes of key processes. The simulations of fat metabolism were carried with a constant input of non-esterified fatty acids (NEFA) from plasma. The fed state and fasted states were characterised by changing this input. Likewise, the simulations of glutathione metabolism were carried out using a constant input of cysteine and glutamate and those of the energy metabolism were carried out using a constant intracellular concentration of glucose-6-phosphate. The simulations of the cholestasis module were carried out using a constant influx of cholic acids. These results are summarized in Tables 2 and 3. The simulated values were calculated after solving the ODEs using MATLAB™ till steady state was obtained. There is good agreement between the literature-reported levels of several metabolites and the model predictions. Overall, the model is able to represent the basic energetics of the hepatocyte correctly as well as the partitioning of the energy production between cytoplasmic and mitochondrial sources. We can see that the effect of nutrient input on fat metabolism is captured well. The model is able to predict the values of ketone-body production as well as the partitioning between esterification and oxidation under fed and fasted conditions. The major hepatocellular antioxidant, glutathione and the primary reactive oxygen species, ROS, that it neutralizes, hydrogen peroxide, are also observed in the right concentration range.

TABLE 2

Concentrations of metabolites of fatty acid oxidative pathway and their comparison with literature values

|  | Simulated value | Experimental value |
|---|---|---|
| Fed State | | |
| Fraction of fatty acids influx in oxidation | 28% | 34% |
| Acetoacetate (Mitochondrial) | 159 μM | 104-217 μM |
| Betahydroxybutyrate (Mitochondrial) | 219 μM | 169-300 μM |
| Acetyl CoA (Mitochondrial) | 62 μM | 33-67 μM |
| Fasted State | | |
| Fraction of fatty acids influx in oxidation | 70% | 70% |
| Acetoacetate (Mitochondrial) | 930 μM | 1040-1648 μM |
| Betahydroxybutyrate (Mitochondrial) | 3930 μM | 3700-4048 μM |
| Acetyl CoA (Mitchondrial) | 116 μM | 91-200 μM |

TABLE 3

Comparison of the simulations of metabolite concentrations and fluxes with their experimental values

| Metabolite | Simulated value | Experimental value |
|---|---|---|
| GSH (mitochondrial) | 10.9 mM | 11 mM |
| GSH (cytosolic) | 7.96 mM | 5-10 mM |
| $H_2O_2$ | $1.0 \times 10^{-5}$ mM | $10^{-4}$-$10^{-6}$ mM |
| ATP (mitochondrial) | 9.0 mM | 10.38 mM |
| ATP (cytosolic) | 2.95 mM | 2.76 mM |
| ADP (mitochondrial) | 7 mM | 5.38 mM |
| ADP (cytosolic) | 0.2 mM | 0.315 mM |
| Phosphate (mitochondrial) | 14 mM | 16.8 mM |
| Phosphate (cytosolic) | 3.375 mM | 3.340 mM |
| ATP from glycolysis | 33% | 38% |
| ATP from oxidative phosphorylation | 66% | 57% |

Example: 3

Adaptability of Cellular ATP Production

The lipid-rich mitochondrial membrane has been recognized as one of the preferred targets for drug molecules or their metabolites, presumably due to their lipophilicity. Impairment of mitochondrial function has been observed due to the treatment of non-steroidal anti-inflammatory drugs (NSAID). Due to the key role played by this membrane in the maintenance of electrochemical potential and hence in ATP synthesis via oxidative phosphorylation by fof1 ATP synthase activity, it is plausible that mitochondrial dysfunction can predispose the cell to ATP depletion and hence necrotic damage. Under normal conditions glycolysis produces only a third of cellular ATP, although there is some redundancy inbuilt in the system. Due to this adaptability, when there is an inhibition in mitochondrial synthetic capacity, glycolysis shows significant up-regulation. We mimicked this effect by decreasing the effective concentration or $V_{max}$ of fof1 ATP synthase. The reduction in ATP generation by the mitochondria is compensated for by an autoupregulation in glycolysis, which is shown in FIG. 1. These results are in agreement with literature. However, the ability to compensate is limited and significant levels of such mitochondrial inhibition can eventually lead to ATP depletion, as is also seen from FIG. 1. These results are in concordance with the observation that many drugs which induce necrosis lead to selective loss of cells in the perivenous area, which is characterized by low oxygen concentrations and high drug metabolism activity.

Example: 4

Ability to Predict the Evolution of Cholestasis

Cholestasis is a complex process that eventually results in the accumulation of bile salts in the blood and its excretion in the urine. Earlier studies have attempted to correlate the cholestatic potential of compounds with their capacity to inhibit the bile salt export pump, BSEP present in canalicular vesicles. Although BSEP is a major contributor to the process of bile efflux and whose disruption can indeed cause cholestasis, other phenomena such as the ones highlighted in Table 1 also need to be considered in order to make physiologically relevant predictions. We carried out a simulation of bile-duct ligation in vivo by setting the $V_{max}$ of the transporter to zero. The results are shown in FIG. 2. The initial rise of taurocholic acid (TCA) in blood followed by gradual and partial recovery of the system is clearly demonstrated here and the results are in accordance with the in vivo observations reported in literature. Here we would like to reiterate that the complexity involved in the evolution of a disease process and its subsequent recovery cannot be predicted by any single in vitro test and requires the understanding and integration of insights from several processes acting in concert.

Example: 5

Effect of Vasopressin on Canalicular Contractility

As said earlier, bile flow is a complex physiological process under rigorous hormonal control. The contractility of the canaliculus was mimicked using a physiological range of vasopressin (0.008-0.012 µM). As can be seen in FIG. 3, increased levels of vasopressin result in an increase in the intracellular calcium amplitude thereby increasing the contractility of the canaliculus. These results are in agreement with experimental observations reported in literature. The simulations were carried out starting from normal serum vasopressin concentration of 0.008 µM which produces a physiological contraction frequency of once in 50s.

Example: 6

Effect of Exposure to Drugs and Toxins

Several drugs and toxins with known mechanisms of perturbation were tested using the model. It is known that oxidative stress is a major cause of necrosis in the liver. Excessive conjugation is one route by which glutathione (GSH), a key cellular antioxidant is depleted leading to the onset of necrosis. FIG. 4 details the effect of ethacrynic acid exposure on the levels of cellular glutathione. Ethacrynic acid is known to be detoxified by glutathione conjugation. The simulation was carried out by increasing the activity of glutathione S transferase ($V_{GST}$). The results are in excellent agreement with literature values not only in the level of GSH, but also in the dynamics of its change in the cell. Perturbations such as decreased GSH synthesis were also carried out using BSO, an inhibitor of GSH synthesis, wherein the activity of $V_{GCS}$ was set to zero, and the results found to be in agreement in literature. These effects of drugs are summarized in Table 4. Daphnetoxin is a known inhibitor of ATP synthesis, which acts by inhibiting fof1 ATPase. The effect of this was simulated by decreasing the rate of fof1 ATPase by the extent shown in the literature. Likewise, the effect of Amiodarone and perhexylline were simulated by decreasing $V_{CPT1}$ as reported in literature

TABLE 4

Instances of model validation on drug exposure

| Drug exposure | Model output monitored | Enzyme affected | Simulation Result | Experiment |
|---|---|---|---|---|
| Buthionine sulfoximine | Half-life GSH depletion | Gamma glutamyl cysteine synthase | 200 min | 120 min |
| Daphnetoxin | EC value | $F_oF_1$ ATPase | 0.53 | 0.52 |
| Perhexilline | Triglyceride accumulation | CPT1 | 92% | 98% |
| Amiodarone | Triglyceride accumulation | CPT1 | 169% | 150% |

Abbreviations: CPT1—carnitine Palmitoyl transferase 1; GSH—glutathione, EC—Energy Charge (indication of cellular energy status)

Example: 7

Discerning Sources of Idiosyncratic Toxicity

FIG. 5 demonstrates another important application of the systems approach. A thought experiment was carried out to understand the range of hydrogen peroxide production rates that can be tolerated by the liver. Since the glutathione reductase activity enables the maintenance of glutathione levels, its activity was also varied simultaneously. The model predicted the effect of this combined variation on the time taken to deplete cellular glutathione. What is informative is that there exists a continuum of intermediate depletion times and hence presumably, glutathione levels as well. The results correlate well with the observation that variations in superoxide dismutase (the in vivo generator of hydrogen peroxide) and glutathione reductase are correlated with the predisposition to liver disease. Similar analysis on other model components is likely to uncover novel sources of variations that could form the basis for idiosyncratic toxicity.

Example: 8

Real-Life Applications of the Model

According to our model, the homeostatic state of the cell with respect to any state variable is determined by the combined effect of various enzymatic/transporter fluxes. We postulate that drugs cause alterations in these fluxes. A quantitative measurement of the fluxes with drugs needs to be carried out and fed into the model in order to get testable outcomes.

Example: 9

The Ability of this Approach to Interface with "Omics" Data

Our systems approach used in conjunction with assays which yield the degree of alteration of enzyme activity can result in the prediction of testable hypotheses. It is also possible to integrate "omic" data, and postulate likely outcomes. FIG. 6 is an illustration of this application. Microarray expression data (personal communications) obtained from rats exposed to amiodarone was analysed to select a differentially expressed gene set. This list included key enzymes of lipid metabolism. For the purposes of the simulation, we assumed that the fold changes in mRNA levels are equal to the changes in corresponding protein activities. Thus, the microarray experiment gives an approximate estimate of altered fluxes of the corresponding enzymes. Using the mRNA levels of acetyl CoA carboxylase (ACC), fatty acid synthase (FAS), acyl CoA synthetase (ACS) and carnitine palmitoyl transferase (CPT1A), representing changes in various processes involved in lipid metabolism as inputs to our model we predicted the fold change in level of triglycerides. To do this, we assumed the level of triglycerides in the untreated sample to be unity. The results are in good agreement with experimental measurements conducted with amiodarone, indicating that our model can also utilize high-throughput microarray data as input and predict testable experimental outcomes.

Example: 10

Handling Individual Variations in Drug Response

The variations in drug response can result from two major sources—from enzymes in the basic biochemistry or the drug metabolizing machinery per se. To estimate the individual's response to a particular drug, then the knowledge of the source of variation is of primary importance. For example, the individual could have lowered glutathione reductase activity. This altered flux can then be used as input to the model. Likewise, any other change in activity of an enzyme can be incorporated into the model. If the individual is known to metabolize drugs differently compared to the "average" individual, the difference in activity of the metabolizing enzymes compared to the basal activity can be used as input to the model.

The set of 112 coupled differential and algebraic equations listed out below describe the system of equations required to represent the liver cell homeostasis with respect to energy, fat, antioxidant and bile metabolism and transport.

Equations of Energy metabolism
Differential equations:
Reactions in cytosol $$d/dt[F1,6P2]_c = V_{PFK} - V_{ALD} \quad \text{(i)}$$

$$d/dt[G3P]_c = 2*V_{ALD} - V_{GPDH} \quad \text{(ii)}$$

$$d/dt[BPG]_c = V_{GPDH} - V_{PGK} \quad \text{(iii)}$$

$$d/dt[PEP]_c = V_{PGK} - V_{PK} \quad \text{(iv)}$$

$$d/dt[Pi]_c = V_{ute} - V_P - V_{PK} - V_{PGK} \quad \text{(v)}$$

$$d/dt[ATP]_c = V_{PK} + V_{PGK} - 2*V_{PFK} + V_{ANT}*(1/Rcm) + V_{ADK} - V_{ute} \quad \text{(vi)}$$

$$d/dt[ADP]_c = V_{ute} - V_{PK} - V_{PGK} + 2*V_{PFK} - V_{ANT}*(1/Rcm) - 2*V_{ADK} \quad \text{(vii)}$$

Reactions in Mitochondria $$d/dt[ATP]_m = V_{fof1} - V_{ANT} \quad \text{(viii)}$$

$$d/dt[NADH]_m = -V_{res} + V_{DH} \quad \text{(ix)}$$

$$d/dt\Delta\Psi = (V_{res\_H} - V_{fof1\_H} - V_{ANT} - V_{leak} - 3*V_{uni})/C\_{mito} \quad \text{(x)}$$

Algebraic Equations:

$$ATP_c + ADP_c + AMP_c = \text{constant} \quad \text{(xi)}$$

$$ATP_m + ADP_m = \text{constant} \quad \text{(xii)}$$

$$NADH_m + NAD_m = \text{constant} \quad \text{(xiii)}$$

$$3*ATP_c + 2*ADP_c + AMP_c + P_{ic} + (3*ATP_m + 2*ADP_m + P_{im})/Rcm = \text{constant}. \quad \text{(xiv)}$$

Key to abbreviations:
V refers to the physiological rate of the reaction or process and subscript refers either to the enzymes catalyzing the reaction or the name of the transporters; subscripts c and m refer to cytosol and mitochondria respectively. Rcm=cellvolume/mitochondrial volume. ATP—adenosine triphosphate, ADP—adenosine diphosphate, NADH—reduced nicotinamide adenine dinucleotide, $\Delta\Psi$—mitochondrial membrane potential, ALD—Aldolase, PGK—phosphoglycerate kinase, PFK—phosphofructokinase, PK—Pyruvate kinase, ANT—adenine nucleotide translocase, fof1—fof1 ATP synthase, ADK—adenylate kinase, ute—cytosolic utilization of ATP, $V_{leak}$—rate of proton leak, $V_{res}$—rate of respiration (Complex I).

Equations of Glutathione Metabolism
Reactions in the Cytosol $$d/dt[\gamma\text{-}GC] = V_{GCS} - V_{GS} \quad \text{(xv)}$$

$$d/dt[GSH] = V_{GS} + V_{GR} - 2 \times V_{GPx} - V_{GSH\ efflux\ to\ sinusoid} - V_{GSH\ efflux\ to\ canaliculus} - V_{GST} + V_{GSH\ transport\ from\ mitochondria\ to\ cytosol}/Rcm - V_{GSH\ transport\ from\ cytosol\ to\ mitochondria} \quad \text{(xvi)}$$

$$d/dt[GSSG] = V_{GPx} - V_{GR}/2 - V_{GSSG\ efflux\ to\ canaliculus} \quad \text{(xvii)}$$

$$d/dt[H_2O_2] = V_{H2O2prod} - V_{GPx} \quad \text{(xviii)}$$

Reactions in the Mitochondria $$d/dt[GSH] = V_{GR} - 2 \times V_{GPx} - V_{GST} - V_{GSH\ transport\ from\ mitochondria\ to\ cytosol} + Rcm \times V_{GSH\ transport\ from\ cytosol\ to\ mitochondria} \quad \text{(xix)}$$

$$d/dt[GSSG] = V_{GPx} - V_{GR}/2 \quad \text{(xx)}$$

$$d/dt[H_2O_2] = V_{H2O2prod} - V_{GPx} \quad \text{(xxi)}$$

Key to abbreviations:
V refers to the physiological rate of the reaction or process and subscript refers either to the enzymes catalyzing the reaction or the name of the process; GSH—glutathione, GSSG—oxidized glutathione, GPx—glutathione peroxidase, $\gamma$-GC—gamma glutamyl cysteine, GCS—gamma glutamyl cysteine synthetase, $V_{H2O2prod}$—rate of hydrogen peroxide production, GS—glutathione synthase, GR—glutathione reductase.

Equations of Fatty Acid Metabolism $$d/dt[\text{Palmitate}]_c = V_{influx} + V_{FAS} - V_{FACS} \quad \text{(xxii)}$$

$$d/dt[\text{PalmitoylCoA}]_c = V_{FACS} - V_{CPT1} - V_{GPATm} - V_{ACAT} - V_{LPAT} - V_{DGAT} \quad \text{(xxiii)}$$

$$d/dt[\text{Palmitoylcarnitine}]_m = Rcm*V_{CPT1} - V_{CPT2} \quad \text{(xxiv)}$$

$$d/dt[\text{PalmitoylCoA}]_m = V_{CPT2} - V_{AcylCoAdehydrogenase} \quad \text{(xxv)}$$

$$d/dt[\text{EnoylCoA}]_m = V_{AcylCoAdehydrogenase} - V_{EnoylCoAhydratase} \quad \text{(xxvi)}$$

$$d/dt[\text{HydroxyacylCoA}]_m = V_{EnoylCoAhydratase} - V_{HydroxyacylCoAdehydrogenase} \quad \text{(xxvii)}$$

$$d/dt[\text{ketoacylCoA}]_m = V_{HydroxyacylCoAdehydrogenase} - V_{AcetyCoAacetyltransferase} \quad \text{(xxviii)}$$

$$d/dt[\text{AcetylCoA}]_m = 8*(V_{AcetyCoAacetyltransferase}) - V_{CS} - 2*V_{Acetoacetyltransferase} - V_{HMGSYN} + V_{HMGLYASE} \quad \text{(xxix)}$$

$$d/dt[\text{AcetoacetylCoA}]_m = V_{Acetoacetyltransferase} - V_{HMGSYN} \quad \text{(xxx)}$$

$$d/dt[\text{Hydroxymethylglutarate CoA}]_m = V_{HMGSYN} - V_{HMGLYASE} \quad \text{(xxxi)}$$

$$d/dt[\text{Acetoacetate}]_m = V_{HMGLYASE} - V_{Hydroxybutyratedehydrogenase} - V_{efflux\_acetoacetate} \quad \text{(xxxii)}$$

$$d/dt[\text{Hydroxybutyrate}]_m = V_{Hydroxybutyratedehydrogenase} - V_{efflux\_hydroxybutyrate} \quad \text{(xxxiii)}$$

$$d/dt[sn1\text{palmitoylglycerol3phosphate}]_c = V_{GPAT} - V_{LPAT} \quad \text{(xxxiv)}$$

$$d/dt[sn12\text{dipalmitoylglycero3phospahte}]_c = V_{LPAT} - V_{PAP} \quad \text{(xxxv)}$$

$$d/dt[\text{Dipalmitoylglycerol}]_c = V_{PAP} - V_{DGAT} - V_{DCPT} \quad \text{(xxxvi)}$$

$$d/dt[\text{Triglycride}]_c = V_{DGAT} - V_{TGSEC} \quad \text{(xxxvii)}$$

$$d/dt[\text{Phosphatidylcholine}]_c = V_{DCPT} - V_{PLSEC} \quad \text{(xxxviii)}$$

$$d/dt[\text{MalonylCoA}]_c = V_{ACC} - 7^*V_{FAS} - V_{MYD} \quad \text{(xxxix)}$$

Key to abbreviations

V refers to the physiological rate of the reaction or process and subscript refers either to the enzymes catalyzing the reaction or the name of the process; subscripts c and m refer to cytosol and mitochondria respectively.

Influx=Transport of fatty acids from plasma to the hepatocyte, FAS—Fatty acid synthase, ACS—Fatty acyl CoA synthase, GPAT—MitochondrialGlycerol-3-phosphate O-acyltransferase, ACAT—acyl-CoA: cholesterol acyltransferase, LPAT—1-acylglycerol-3-phosphate O-acyltransferase, DGAT—diacylglycerol O-acyltransferase, CPT1—Carnitine O-palmitoyltransferaseI, CPT2—Carnitine O-palmitoyltransferase, CS—Citrate synthase, HMGSYN—Hydroxymethylglutaryl CoA synthase, HMGLYASE—Hydroxymethylglutaryl CoA lyase, Efflux_acetoacetate—Transport of betahydroxybutyrate from hepatocyte to the plasma, Efflux_hydroxybutyrate—Transport of betahydroxybutyrate from hepatocyte to the plasma, PAP—Phosphatidate phosphatase, DCPT—diacylglycerol cholinephosphotransferase, TGSEC—Transport of triglyceride from the hepatocyte to the plasma, PCSEC—Transport of phosphatidylcholine from hepatocyte to plasma.

Equations of Bile Salt Metabolism and Transport $$d/dt[CA]_{blood} = V_{reabsorption\_int} + V_{reflux} - V_{uptake} - [GFR - V_{renal\ reabsorption}]/0.02 \quad \text{(xl)}$$

$$d/dt[TCA]_{blood} = V_{reabsorption\_int} + V_{reflux} - V_{uptake} - [GFR - V_{renal\ reabsorption}]/0.02 \quad \text{(xli)}$$

$$d/dt[CA]_h = V_{synthesis} + V_{uptake} - V_{conjugation} - V_{reflux} \quad \text{(xlii)}$$

$$d/dt[TCA]_h = V_{conjugation} + V_{uptake} - V_{reflux} - V_{secretion} - V_{sulphation} \quad \text{(xliii)}$$

$$d/dt[TCA]_{bile} = V_{secretion} \quad \text{(xliv)}$$

$$d/dt[CA]_{urine} = [GFR - V_{renal\ reabsorption}] \quad \text{(xlv)}$$

$$d/dt[TCA]_{urine} = [GFR - V_{renal\ reabsorption}] \quad \text{(xlvi)}$$

Key to abbreviations:

V refers to the physiological rate of the process, subscripts indicate compartments or process. CA—cholic acid, TCA—taurocholic acid, $[\text{metabolite}]_{blood}$=concentration of the metabolite in the blood, $[\text{metabolite}]_h$=concentration of the metabolite in the hepatocyte, $[\text{metabolite}]_{bile}$=concentration of the metabolite in bile, $[\text{metabolite}]_{urine}$=concentration of the metabolite in the urine, GFR=glomerular filtration rate. Reflux—movement of bile salts from hepatocyte to blood, uptake—movement of bile salts from blood to hepatocyte, synthesis—synthesis of cholic acid from cholesterol in the hepatocyte, conjugation—amidation of cholate to taurocholate, secretion—secretion of bile salts into the canaliculus to form bile, sulphation—the conversion of taurocholate to taurocholate sulphate, renal reabsorption—the reabsorption of bile salts by the kidney.

Equations of Canalicular Contraction $$d/dt[\text{Gactin}] = -V_{Gactin.ATP} - V_{Gactin.ADP} - V_{Gactin.Profilin} - V_{Gactin.Thymosin} \quad \text{(xlvii)}$$

$$d/dt[ATP.\text{Gactin}] = V_{Gactin.ATP} - V_{Gactin.ATP.Profilin} - V_{Gactin.ATP.Thymosin} - V_{polyGactin.ATP\_barbed} - V_{polyGactin.ATP\_pointed} + V_{depolyGactin.ATP\_barbed} + V_{depolyGactin.ATP\_pointed} \quad \text{(xlviii)}$$

$$d/dt[ATP.\text{Gactin}] = V_{Gactin.ADP} - V_{Gactin.ADP.Profilin} - V_{Gactin.ADP.Thymosin} - V_{polyGactin.ADP\_barbed} - V_{polyGactin.ADP\_pointed} + V_{depolyGactin.ADP\_barbed} + V_{depolyGactin.ADP\_pointed} \quad \text{(xlix)}$$

$$d/dt[\text{thymosin.Gactin}] = V_{Gactin.Thymosin} - V_{Gactin.Thymosin.ATP} - V_{Gactin.Thymosin.ADP} \quad \text{(l)}$$

$$d/dt[ATP.\text{Gactin.thyb4}] = V_{Gactin.ATP.Thymosin} + V_{Gactin.Thymosin.ATP} \quad \text{(li)}$$

$$d/dt[ADP.\text{Gactin.thyb4}] = V_{Gactin.ADP.Thymosin} + V_{Gactin.Thymosin.ADP} \quad \text{(lii)}$$

$$d/dt[\text{profilin.Gactin}] = V_{Gactin.Profilin} - V_{Gactin.Profilin.ATP} - V_{Gactin.Profilin.ADP} \quad \text{(liii)}$$

$$d/dt[ATP.\text{Gactin.profilin}] = V_{Gactin.ATP.Profilin} + V_{Gactin.Profilin.ATP} - V_{Profilin.polyGactin.ATP\_barbed} \quad \text{(liv)}$$

$$d/dt[ADP.\text{Gactin.profilin}] = V_{Gactin.ADP.Profilin} + V_{Gactin.Profilin.ADP} - V_{Profilin.polyGactin.ADP\_barbed} \quad \text{(lv)}$$

$$d/dt[\text{num\_of\_barbZ\_ptCapped}] = V_{Zcapping} \quad \text{(lvi)}$$

$$d/dt[\text{num\_of\_barbG\_ptCapped}] = V_{Gcapping} \quad \text{(lvii)}$$

$$d/dt[\text{num\_of\_barbProf\_ptCapped}] = V_{Profilincapping} \quad \text{(lviii)}$$

Note: The actin polymer may get capped by Cap Z, Cap G and Profilin, hence the population of capped actins can be described by (lvi-lviii).

$$d/dt[\text{polymerization\_barbed}] = V_{polyGactin.ATP\_barbed} + V_{polyGactin.ADP\_barbed} + V_{Profilin.polyGactin.ATP\_barbed} + V_{Profilin.polyGactin.ADP\_barbed} \quad \text{(lix)}$$

$$d/dt[\text{depolymerization\_barbed}] = V_{depolyGactin.ATP\_barbed} + V_{depolyGactin.ADP\_barbed} \quad \text{(lx)}$$

$$d/dt[\text{polymerization\_pointed}] = V_{polyGactin.ATP\_pointed} + V_{polyGactin.ADP\_pointed} \quad \text{(lxi)}$$

$$d/dt[\text{depolymerization\_pointed}] = V_{depolyGactin.ATP\_pointed} + V_{depolyGactin.ADP\_pointed} \quad \text{(lxii)}$$

$$d/dt[\text{growth\_barbed}] = d/dt[\text{polymerization\_barbed}] - d/dt[\text{depolymerization\_barbed}] \quad \text{(lxiii)}$$

$$d/dt[\text{growth\_pointed}] = d/dt[\text{polymerization\_pointed}] - d/dt[\text{depolymerization\_pointed}] \quad \text{(lxiv)}$$

$$d/dt[\text{net\_growth\_of\_filaments}] = d/dt[\text{growth\_barbed}] + d/dt[\text{growth\_pointed}] \quad \text{(lxv)}$$

Note: Polymerization at barbed/pointed-end involves appending either ATP or ADP actin at that end. Depolymerization removes actin from the respective end. Net growth at each end is thus the difference between the rates of polymerization and depolymerization.

$$d/dt[\text{Receptor}] = -V_{Gprotein.Receptor} - V_{Receptor.Ligand} + V_{deg\_Gq11.Receptor} + V_{deg\_GRKmediatedGq11cleavage} \quad \text{(lxvi)}$$

$$d/dt[\text{GProtein}] = -V_{Gprotein.Receptor} - V_{Gprotein.Receptor.Ligand} + V_{deg\_GRKmediatedGq11cleavage} + V_{deg\_Gq11Receptor} \quad \text{(lxvii)}$$

$$d/dt[\text{GProt.Receptor}] = V_{Gprotein.Receptor} - V_{LigandGprotein.Receptor.Ligand} \quad \text{(lxviii)}$$

$$d/dt[\text{Receptor.Ligand}] = V_{Ligand \to ReceptorLigand} - V_{Gprotein.Receptor.Ligand} \quad \text{(lxix)}$$

$$d/dt[\text{GProt.Receptor.Ligand\_inactive}] =$$
$$V_{Gprotein.Receptor.Ligand} + V_{Gprotein.Receptor.Ligand} - $$
$$V_{Gprotein.Receptor.Ligand} + V_{Gprotein.Receptor.Ligand} \quad (\text{lxx})$$

$$d/dt[\text{GProt.Receptor.Ligand\_active}] =$$
$$V_{Gprotein.Receptor.Ligand} + V_{Gprotein.Receptor.Ligand} - $$
$$V_{deg\_Gq11Receptor} - V_{deg\_GRKmediatedGq11cleavage} \quad (\text{lxxi})$$

Note: $V_{deg}$ refers to the rate of degradation. The triple complex of Receptor-Gprotein-Ligand is the active form.

$$d/dt[\text{PLC.beta}] = -V_{PLC.Ca^{2+}} - V_{PLC.Gq11} + V_{deg\_PLC.Gq11.Ca^{2+}} \quad (\text{lxxii})$$

$$d/dt[\text{PLCbeta.Ca}^{2+}] = V_{PLC.Ca^{2+}} - V_{PLC.Ca^{2+}.Gq11} \quad (\text{lxxiii})$$

$$d/dt[\text{PLCbeta.}Gq11.GTP] = V_{PLC.Gq11} - V_{PLC.Gq11.Ca^{2+}} \quad (\text{lxxiv})$$

$$d/dt[\text{PLCbeta.Ca}^{2+}.Gq11.GTP] = V_{PLC.Ca^{2+}.Gq11} + V_{PLC.Gq11.Ca^{2+}} - V_{deg\_PLC.Gq11.Ca^{2+}} \quad (\text{lxxv})$$

Note: The triple complex of PLC-Calcium-Gq11-GTP is the active form $$d/dt[\text{Ca}^{2+}]_c = 2*(-V_{CamC} - V_{CamN} - V_{CamNC} - V_{CamNC} - V_{CamCM} - V_{CamNM} - V_{CamNCM} - V_{CamNCM}) + V_{Ca2+Cytosol} - V_{Ca2+ER} + V_{deg\_PLC.Gq11.Ca2+} \quad (\text{lxxvi})$$

$$d/dt[\text{MLCK}] = -V_{Cam \to CamM} - V_{CamC \to CamCM} - V_{CamN \to CamNM} - V_{CamNC \to CamNCM} \quad (\text{lxxvii})$$

$$d/dt[\text{Cam}] = -V_{seqCam} - V_{CamC} - V_{CamN} - V_{CamM} \quad (\text{lxxviii})$$

$$d/dt[\text{Cam}C] = V_{CamC} - V_{CamCM} - V_{CamNC} \quad (\text{lxxix})$$

$$d/dt[\text{Cam}N] = V_{CamN} - V_{CamNM} - V_{CamNC} \quad (\text{lxxx})$$

$$d/dt[\text{Cam}M] = V_{CamM} - V_{CamCM} - V_{CamNM} \quad (\text{lxxxi})$$

$$d/dt[\text{Cam}NC] = V_{CamNC} + V_{CamNC} - V_{CamNCM} \quad (\text{lxxxii})$$

$$d/dt[\text{Cam}NM] = V_{CamNM} + V_{CamNM} - V_{CamNCM} \quad (\text{lxxxiii})$$

$$d/dt[\text{Cam}CM] = V_{CamCM} + V_{CamCM} - V_{CamNCM} \quad (\text{lxxxiv})$$

$$d/dt[\text{Cam}NCM] = V_{CamNCM} + V_{CamNCM} - V_{CamNCM} \quad (\text{lxxxv})$$

Key to abbreviations: The triple complex of Calmodulin, four Calcium ions and MLCK is the active form. $Ca^{2+}_c$=cytosolic calcium; Cam=Calmodulin, N=2 Calcium ions at N-terminal, C=2 Calcium ions at C-terminal and M=MLCK, myosin light chain kinase.

Equations for Calcium Release from ER Due to Activated PLC $$d/dt[\text{ER\_Ca}] = V_{Ca^{2+}ER} - V_{Ca^{2+}Cytosol} \quad (\text{lxxxvi})$$

$$d/dt[\text{InsP3\_145}] = V_{syn\_IP\_3} - V_{deg\_IP\_3} \quad (\text{lxxxvii})$$

$$d/dt[\text{Cam\_buffer}] = V_{seqCam} \quad (\text{lxxxviii})$$

$$d/dt[\text{PKCalpha/gamma\_inactive}] = -V_{activation\_PKCalpha/gamma} \quad (\text{lxxxix})$$

$$d/dt[\text{PKCalpha/gamma\_active}] =$$
$$V_{activation\_PKCalpha/gamma} - V_{PKCalpha/gamma.DAG} - V_{pKCalpha/gamma.Ca^{2+}} - V_{PKCalpha/gamma.AA} \quad (\text{xc})$$

$$d/dt[\text{PKCalpha/gamma\_DAG}] = V_{PKCalpha/gamma.DAG} - V_{PKCalpha/gamma.DAG.AA} \quad (\text{xci})$$

$$d/dt[\text{DAG}] = V_{syn\_IP3} - V_{PKCalpha/gamma.DAG} - V_{PKCalpha/gamma.Ca^{2+}.DAG} \quad (\text{xcii})$$

$$d/dt[\text{PKCalpha/gamma.Ca}^{2+}] = V_{PKCalpha/gamma.Ca^{2+}} - V_{PKCalpha/gamma.Ca^{2+}.AA} - V_{PKCalpha/gamma.Ca^{2+}.DAG} \quad (\text{xciii})$$

$$d/dt[\text{PKCalpha/gamma.AA}] = V_{PKCalpha/gamma.AA} \quad (\text{xciv})$$

$$d/dt[\text{AA}] = -V_{PKCalpha/gamma.AA} - V_{PKCalpha/gamma.Ca^{2+}.AA} - V_{PKCalpha/gamma.DAG.AA} - V_{activationRhoK\_AA} \quad (\text{xcv})$$

$$d/dt[\text{PKCalpha/gamma.Ca}^{2+}.AA] = V_{PKCalpha/gamma.Ca^{2+}.AA} \quad (\text{xcvi})$$

$$d/dt[\text{PKCalpha/gamma.Ca}^{2+}.DAG] = V_{PKCalpha/gamma.Ca^{2+}.DAG} \quad (\text{xcvii})$$

$$d/dt[\text{PKCalpha/gamma.DAG.AA}] = V_{PKCalpha/gamma.DAG.AA} - V_{PKCalpha/gamma.DAG.AA.Ca^{2+}} \quad (\text{xcviii})$$

$$d/dt[\text{PKCalpha/gamma\_DAG\_AA\_Ca}^{2+}] = V_{PKCalpha/gamma.DAG.AA.Ca^{2+}} \quad (\text{xcix})$$

Note: The complexes of Protein Kinase C (PKC) alpha/gamma, Calcium, DAG (diacylglycerol) and Arachidonic Acid (AA) are active in various combinations. CPI-17 is activated by PKC $$d/dt[\text{CPI\_17\_inactive}] = -V_{activation\_CPI17} + V_{inactivationCPI17} \quad (\text{c})$$

$$d/dt[\text{CPI\_17\_active}] = V_{activation\_CPI17} - V_{inactivationCPI17} - V_{inactivationMLCP\_CPI17} \quad (\text{ci})$$

MLCP is inactivated by CPI-17, RhoA=activated Rho, RhoA.RhoK=RhoKinase activated by RhoA, AA=Arachidonic Acid $$d/dt[\text{MLCP\_active}] = -V_{inactivationMLCP\_CPI17} - V_{inactivationMLCP\_RhoARhoK} - V_{inactivationMLCP\_RhoA} \quad (\text{cii})$$

$$d/dt[\text{MLCP\_CPI17\_inactivated}] = V_{inactivationMLCP\_CPI17} \quad (\text{ciii})$$

$$d/dt[\text{RhoA\_RhoK\_active}] = V_{activationRhoK\_RhoA} - V_{inactivationMLCP\_RhoARhoK} \quad (\text{civ})$$

$$d/dt[\text{RhoK\_active}] = V_{activationRhoK\_AA} - V_{inactivationMLCP\_RhoA} \quad (\text{cv})$$

$$d/dt[\text{MLCP\_RhoARhoK\_inactivated}] = V_{inactivationMLCP\_RhoARhoK} \quad (\text{cvi})$$

$$d/dt[\text{MLCP\_RhoA\_inactivated}] = V_{inactivationMLCP\_RhoA} \quad (\text{cvii})$$

$$d/dt[\text{Rho}] = -V_{Rho\_GTP} \quad (\text{cviii})$$

$$d/dt[\text{RhoA}] = V_{Rho\_GTP} - V_{activationRhoK\_RhoA} \quad (\text{cix})$$

$$d/dt[\text{RhoK\_inactive}] = -V_{activationRhoK\_RhoA} - V_{activationRhoK\_AA} \quad (\text{cx})$$

The kinetics of the above three equations are assumed to be as described here.

Intensity of contraction, an empirical function that we have defined, takes into account four factors namely the MLCP activity, MLCK activity, the amounts of polymer Actin and Myosin.

$$d/dt[\text{intensity of contraction}]= (1-MLCP\_\text{activity})*\text{Myosin2}* (d/dt[\text{net\_growth\_of\_filaments}]+d/dt[\text{Cam}NCM]) \quad \text{(cxi)}$$

The degree of bile propulsion tells the rate at which bile may get cleared from the canaliculi.

$$d/dt[\text{degree\_of\_bile\_propulsion}]=\text{intensity of contraction} \quad \text{(cxii)}$$

Example: 11

Toxicity to Organs Other than the Liver

The model can be applied to prediction of toxicity to other organs such as the kidney. This can be done by first surveying the literature to understand the clinically relevant modes of nephrotoxicity. The biochemical pathways that underlie the health of the kidney cell can then be constructed. Subsequently, the equations in the model need to be modified appropriately to represent the homeostatic state. Following this, perturbations can be carried out in the model using BioLego and a new set of assays designed. The assays can then be performed in cultures of kidney cells and the results fed into BioLego.

Example: 12

For Disease States Other than Toxicity

The liver is an organ with many important functions in the body. The disclosure in the present form addresses the function of the liver as an organ of detoxification. In another application, the model can be used to predict the effect of diet on cardiovascular health. The liver stores and releases excess fat in the form of lipoproteins. An excess of these lipoproteins in the blood predisposes an individual to atherosclerosis. The model (with some modifications) can be made to represent this fat disposal function of the liver. Thus it can help model various pathological states that precipitate atherosclerosis.

To use the present disclosure in the context of other diseases, the core model should be changed to represent the homeostasis relevant to that condition. For example, to predict tumor metabolism the model should be modified to capture the differences in metabolic function in a tumor. Some of the differences are listed below and can be used to modify the existing liver model to represent a tumor.

Enhanced glycolytic capacity since angiogenesis lags behind tumor growth
Presence of embryonic form of pyruvate kinase that preferentially shuttles pyruvate to LDH
Increase in pyruvate kinase activity
ROS induced upregulation of HIF-1
Additional pentoses for rapid DNA synthesis
Increased fatty acid synthesis
Dietary inhibition of FAS is lost due to decrease in angiogenesis
Upregulation of cholesterol synthesis via increases in HMG CoA reductase and LDL receptor with concomitant alterations in serum lipid profiles.
Absence of purine salvage pathway
The loss of zinc uptake function, relieves inhibition leading to a citrate oxidising phenotype that is malignant Example: 13

Our approach is based on understanding the basis of liver homeostasis and its perturbations by drugs is reasonably versatile and accurate. It captures liver physiology well and is also able to depict the effect of a variety of drugs. Since the underlying biochemical framework on which it rests encompasses basic processes within the liver such as antioxidant, bile, energy and nutrient metabolism, it is likely to be comprehensive in its coverage of drug and disease settings. The methodology that has been employed to create this system is generic and can be applied to other organ and physiological systems as well.

There is a dearth of model systems that accurately predict toxicity, particularly idiosyncratic toxicity in humans. Since in vitro systems cannot reproduce variations in biochemistry due to genetic and environmental factors, they are not equipped to handle idiosyncratic toxicity. In our approach since we define the homeostasis or the "starting state" of the liver, it is straightforward to modify the model to represent disease conditions and immunological states. A new state of homeostasis can then be defined to mimic disease-specific and patient-specific effects. Indeed, we postulate that hepatotoxicity is a complex outcome of factors pertaining to drug, disease and patient. This definition therefore treats idiosyncrasy not as an aberration, but as a logical outcome of this complexity. Hence it has the potential to discover novel sources of patient variation as shown by the example in FIG. 5.

In summary, we need to move away from our current state-of-art where toxicology is an observational discipline of effects on animals to one where we can, combining in vitro and in silico approaches, understand the basic mechanisms that lead to evolution of toxicity and subsequently define "confirmatory" experiments that may be more targeted and useful. Our approach is a step in this direction and shows the potential of being able to provide a quantitative and mechanistic assessment of toxic liabilities of chemical entities in the liver.

We claim:

1. A computer readable non-transitory storage medium or media for in silico modeling and prediction of drug induced toxicity in the liver, comprising:
(a) a data structure contained on a computer readable storage medium or media that is read by a computer, said data structure comprising:
(i) a database comprising list of drug induced liver disorders and toxic endpoints thereof;
(ii) a database comprising molecular mechanisms and biochemical pathways corresponding to said disorders;
(iii) a database comprising biomolecules for modeling of kinetics of enzymes corresponding to said molecular mechanisms and biochemical pathways;
(iv) a database comprising nonlinear ordinary differential and algebraic equations required to represent the dynamics and steady states corresponding to said biomolecules and enzymes, wherein said nonlinear ordinary differential and algebraic equations comprise equations (i), (ii), (iii), (iv), (v), (vi), (vii), (viii), (ix), (x), (xi), (xii), (xiii), (xiv), (xv), (xvi), (xvii), (xviii), (xix), (xx), (xxi), (xxii), (xxiii), (xxiv), (xxv), (xxvi), (xxvii), (xxviii), (xxix), (xxx), (xxxi), (xxxii), (xxxiii), (xxxiv), (xxxv), (xxxvi), (xxxvii), (xxxviii), (xxxix), (xl), (xli), (xlii), (xliii), (xliv), (xlv), (xlvi), (xlvii), (xlviii), (xlix), (l), (li), (lii), (liii), (liv), (lv), (lvi), (lvii), (lviii), (lix), (lx), (lxi), (lxii), (lxiii), (lxiv), (lxv), (lxvi), (lxvii), (lxviii), (lxix), (lxx), (lxxi), (lxxii), (lxxiii), (lxxiv), (lxxv), (lxxvi), (lxxvii), (lxxviii), (lxxix), (lxxx), (lxxxi), (lxxxii), (lxxxiii), (lxxxiv), (lxxxv), (lxxxvi), (lxxxvii), (lxxxviii), (lxxxix), (xc), (xci), (xcii), (xciii), (xciv), (xcv), (xcvi), (xcvii), (xcviii), (xcix), (c), (ci), (cii), (ciii), (civ), (cv), (cvi), (cvii), (cviii), (cix), (cx), (cxi), and (cxii);

(b) a program contained on said computer readable storage medium or media comprising executable commands using said data structure for determining steady state levels of said biomolecules based on the kinetics of the enzymes in said molecular mechanisms and biochemical pathways;

(c) a program contained on said computer readable storage medium or media comprising executable commands using said data structure for feeding data set obtained by in vitro assays, wherein the data set represents the interaction of said drug with liver;

(d) a program contained on said computer readable storage medium or media comprising executable commands using said data structure for perturbing the steady state levels of said biomolecules based on the data set; and (e) said program contained on said computer readable storage medium or media comprising executable commands for correlating the perturbations to said toxic endpoints and visually displaying at least one steady state level of the key biomolecule and the perturbation for the prediction of drug induced toxicity in liver.

2. The computer readable non-transitory medium or media of claim 1, wherein the liver disorder or the toxic end point is caused by perturbations in the molecular mechanisms and biochemical pathways corresponding to energy metabolism, glutathione metabolism, lipid metabolism, bile salt metabolism and canalicular contractions or any combination thereof.

3. The computer readable non-transitory medium or media of claim 1, wherein the determination of steady state levels of the biomolecules provides an in silico homeostatic model.

4. The computer readable non-transitory medium or media of claim 1, wherein the drug when contacted with the liver produces changes in functioning of the enzymes.

5. The computer readable non-transitory medium or media of claim 4, wherein the changes are measured by in-vitro assays to generate data set used as an input to the in silico homeostatic model.

6. The computer readable non-transitory medium or media of claim 5, wherein the input is a perturbation of the in silico homeostatic model.

7. The computer readable non-transitory medium or media of claim 6, wherein the perturbation in the in silico homeostatic model mimics interaction of the drug with the liver and results in an output.

8. The computer readable non-transitory medium or media of claim 7, wherein the output provides modulation in molecular mechanisms, biochemical pathways and kinetics of the enzymes to predict the toxicity of the drug.

* * * * *